United States Patent [19]
Claremon et al.

[11] Patent Number: 5,691,332
[45] Date of Patent: Nov. 25, 1997

[54] N-(2,4-DIOXO-2,3,4,5-TETRAHYDRO-1H-1,5-BENZODIAZEPIN-3-YL)-3-AMIDES

[75] Inventors: David A. Claremon, Maple Glen; Roger M. Freidinger, Lansdale; Nigel Liverton, Harleysville; Harold G. Selnick, Ambler; Garry R. Smith, East Norriton, all of Pa.

[73] Assignee: Merck & Co., Inc., Rahway, N.J.

[21] Appl. No.: 699,177

[22] Filed: Aug. 19, 1996

Related U.S. Application Data

[63] Continuation of Ser. No. 476,298, Jun. 7, 1995, abandoned.
[51] Int. Cl.$^6$ .................. A61K 31/55; C07D 281/10
[52] U.S. Cl. .................. 514/221; 540/517; 540/567
[58] Field of Search .................. 540/517, 567; 514/221

[56] References Cited

U.S. PATENT DOCUMENTS

| | | | |
|---|---|---|---|
| 4,470,988 | 9/1984 | Watthey | 540/523 |
| 4,473,575 | 9/1984 | Watthey | 540/523 |
| 4,503,060 | 3/1985 | Walther et al. | 514/214 |
| 4,507,313 | 3/1985 | Braestrap et al. | 514/220 |
| 4,537,885 | 8/1985 | Watthey | 514/183 |
| 4,600,534 | 7/1986 | Bach et al. | 540/523 |
| 4,692,522 | 9/1987 | Parsons et al. | 540/523 |
| 4,775,671 | 10/1988 | Hunkeler et al. | 514/220 |
| 4,820,834 | 4/1989 | Evans et al. | 540/504 |
| 4,847,248 | 7/1989 | Freidinger et al. | 540/563 |
| 4,992,437 | 2/1991 | Naka et al. | 540/503 |
| 5,004,741 | 4/1991 | Evans et al. | 514/221 |
| 5,055,464 | 10/1991 | Murakami et al. | 540/517 |
| 5,166,151 | 11/1992 | Freidinger et al. | 514/215 |
| 5,206,234 | 4/1993 | Bock et al. | 514/213 |
| 5,220,018 | 6/1993 | Bock et al. | 540/509 |
| 5,302,591 | 4/1994 | Fletcher et al. | 514/221 |
| 5,324,726 | 6/1994 | Bock et al. | 514/221 |
| 5,338,861 | 8/1994 | Botta et al. | 548/552 |
| 5,360,802 | 11/1994 | Chambers et al. | 514/211 |
| 5,410,049 | 4/1995 | Chambers | 540/504 |
| 5,426,185 | 6/1995 | Baldwin et al. | 540/509 |
| 5,428,157 | 6/1995 | Baldwin et al. | 540/504 |
| 5,438,055 | 8/1995 | Baldwin et al. | 514/221 |
| 5,439,905 | 8/1995 | Naka et al. | 514/220 |
| 5,439,906 | 8/1995 | Bock et al. | 514/220 |
| 5,504,077 | 4/1996 | Collins et al. | 514/211 |

FOREIGN PATENT DOCUMENTS

| | | | |
|---|---|---|---|
| 1 190 708 | 8/1981 | Canada | G02C 7/04 |
| 0 107 095 A1 | 9/1982 | European Pat. Off. | C07D 227/10 |
| 0 514 133 A1 | 5/1991 | European Pat. Off. | 540/509 |
| 0 538 945 A1 | 10/1991 | European Pat. Off. | 540/509 |
| 0 566 175 A2 | 3/1992 | European Pat. Off. | C07D 307/58 |
| WO 93/02078 | 7/1991 | WIPO | 540/509 |
| WO 93/07131 | 10/1991 | WIPO | 540/509 |
| WO 93/15068 | 1/1992 | WIPO | C07D 311/58 |
| WO 93/17011 | 2/1992 | WIPO | 540/509 |
| WO 93/19063 | 3/1992 | WIPO | 540/509 |
| WO 93/08176 | 7/1992 | WIPO | 540/509 |
| WO 94/05673 | 8/1992 | WIPO | 540/503 |

OTHER PUBLICATIONS

J. Gen. Physiol., vol. 96, pp. 195–215 (Jul. 1990), by M. C. Sanguinetti, et al.

J. Cardiovasc. Pharmacol., vol. 20, (Suppl. 2) pp. S17–S22 (1992), by L. M. Hondeghem.

*Primary Examiner*—Robert T. Bond
*Attorney, Agent, or Firm*—Elliott Korsen; Frances P. Bigley; Mark R. Daniel

[57] ABSTRACT

This invention is concerned with novel compounds represented by structural formula I

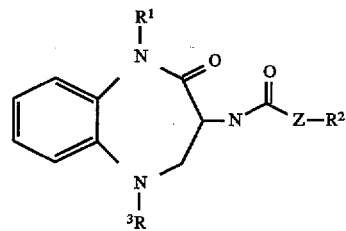

FORMULA I which are useful in the treatment of arrhythmia.

21 Claims, No Drawings

N-(2,4-DIOXO-2,3,4,5-TETRAHYDRO-1H-1,5-BENZODIAZEPIN-3-YL)-3-AMIDES

This is a continuation of application Ser. No. 08/476,298 filed on Jun. 7, 1995 now abandoned.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, agents which exhibit both satisfactory effects and high safety profiles have not been marketed. For example, antiarrythmic agents of Class I, according to the classification of Vaughan-Williams, which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drags which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formula I

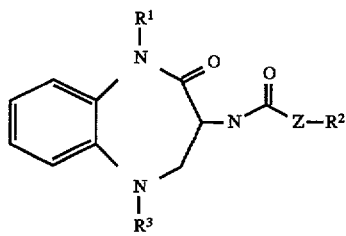

FORMULA I where $R^1$ and $R^3$ are independently $C_{1-6}$ alkyl branched chain; substituted $C_{1-6}$ alkyl, either straight or branch chain wherein the substitutents are selected from F, $C_{3-8}$ cycloalkane, —OH, —$CF_3$, and Z is
1) $C_{1-6}$ alkyl straight or branched chain,
2) substituted $C_{1-6}$ alkyl, either straight or branch chain, wherein the substitutents are selected from F, —OH, $NO_2$,
3) $C_{2-4}$ alkenylene, either straight or branch chain,
4) —$(CH_2)_m$—W—$(CH_2)_n$— wherein m and n are independently 0, 1, 2, 3 or 4 and W is —O—, —S— or —NH,
5) $C_{3-6}$ cycloalkane,
6) $C_{3-6}$ cycloalkylene, or
7) single bond;

$R^2$ is
1) phenyl, either unsubstituted or substituted with one or two substituents selected from
 a) —$NO_2$, —OH,
 b) —Cl, Br, F, or I,
 c) —$CF_3$,
 d) —$C_{1-3}$ alkyl,
 e) —$C_{1-3}$ alkoxy,
 f) —CN,
 g) -methylenedioxy,
2) $C_{5-7}$ cycloalkyl, either unsubstituted or substituted with one or two substitutents selected from
 a) —$NO_2$, OH,
 b) F,
 c) —$CF_3$,
 d) —$C_{1-3}$ alkyl,
 e) —$C_{1-3}$ alkoxy,
 f) —CN,
 g) -methylenedioxy, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment.

DETAILED DESCRIPTION OF THE INVENTION

The novel compounds of this invention have structural formulae

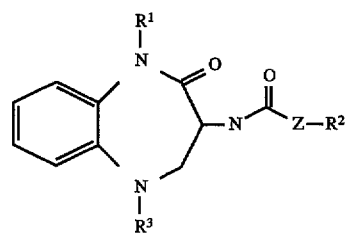

FORMULA I where $R^1$ and $R^3$ are independently $C_{1-6}$ alkyl branched chain; substituted $C_{1-6}$ alkyl branched chain wherein the substitutents are selected from F, $C_{3-8}$ cycloalkane, —OH, —$CH_3$, [Hal please expand] and Z is
1) $C_{1-6}$ alkyl, either straight or branch chain,
2) substituted $C_{1-6}$ alkyl, either straight or branch chain, wherein the substitutents are selected from F, —OH, $NO_2$,
3) $C_{2-4}$ alkenylene, either straight or branch chain,
4) —$(CH_2)_m$—W—$(CH_2)_n$— wherein m and n are independently 0, 1, 2, 3 or 4 and W is —O—, —S— or —NH, 4) $C_{3-6}$ cycloalkane, 5) $C_{3-6}$ cycloalkylene, or 6) single bond;

$R^2$ is 1) phenyl, either unsubstituted or substituted with one or two substituents selected from
   a) —$NO_2$, —OH,
   b) —F, —Cl, —Br, —I,
   c) —$CF_3$,
   d) —$C_{1-3}$ alkyl,
   e) —$C_{1-3}$ alkoxy,
   f) —CN,
   g) -methylenedioxy, 2) $C_{5-7}$ cycloalkyl, either unsubstituted or substituted with one or two substitutents selected from
   a) —$NO_2$, —OH,
   b) —F,
   c) —$CF_3$,
   d) —$C_{1-3}$ alkyl,
   e) —$C_{1-3}$ alkoxy,
   f) —CN,
   g) -methylenedioxy, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment. These compounds include pharmaceutically acceptable crystal forms and hydrates of the compounds of Formula I, which are antiarrhythmic agents.

One embodiment of the novel compounds of this invention is N-(2-Oxo-1,5-bis-(2-propyl)-2,3,4,5-tetrahydro-1H-1,5-benzodiazepin-3-yl)-2-(2,4-dichlorophenyl) propionamide.

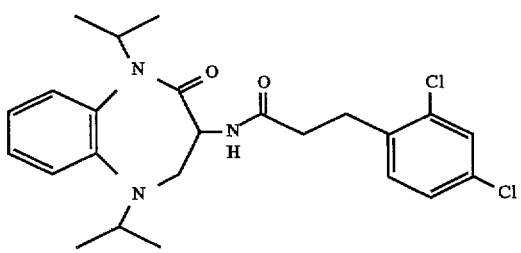

The synthesis of this compound is shown diagramatically in Scheme I and is fully explained in Example 1.

Yet an other embodiment of the novel compounds of this invention is N-(2-Oxo-1,5-bis-(2-propyl)-2,3,4,5-tetrahydro-1H-1,5-benzodiazepin-3-yl)-2-(3,5-dichlorophenyl)acetamide.

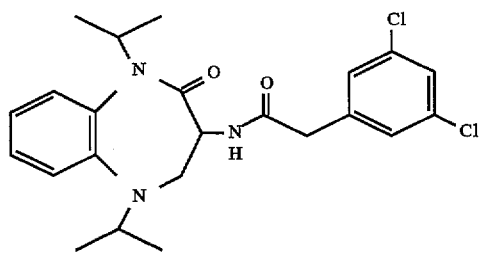

The synthesis of this compound is shown diagramatically in Scheme I and is fully explained in Example 2.

An other embodiment of the novel compounds of this invention is N-(2-Oxo-1,5-bis-(2-propyl)-2,3,4,5-tetrahydro-1H-1,5-benzodiazepin-3-yl)-2-(2,4-dichlorophenyl)acetamide

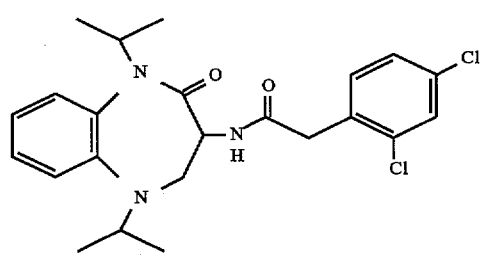

The synthesis of this compound is shown diagramatically in Scheme I and is fully explained in Example 3.

Yet an other embodiment of the novel compounds of this invention is (−)-N-(2-Oxo-1,5-bis-(2-propyl)-2,3,4,5-tetrahydro-1H-1,5-benzodiazepin-3-yl)-2-(2,4-dichlorophenyl)acetamide

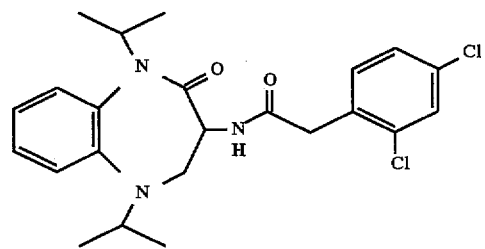

The synthesis of this compound is shown diagramatically in Scheme II and is fully explained in Example 4.

An other embodiment of the novel compounds of this invention is (−)-N-(2-Oxo-1,5-bis-(2-propyl)-2,3,4,5-tetrahydro-1H-1,5-benzodiazepin-3-yl)-2-(3,5-dichlorophenyl)acetamide

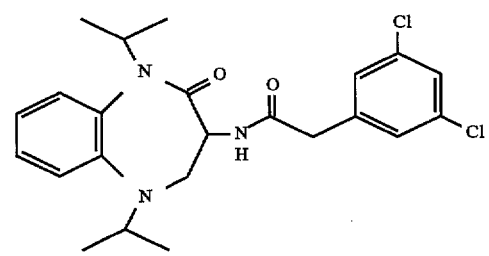

The synthesis of this compound is shown diagramatically in Scheme II and is fully explained in Example 5.

An other embodiment of the novel compounds of this invention is (−)-N-(2-Oxo-1-(2-propyl)-5-(2-propyl)-2,3,4, 5-tetrahydro-1H-1,5-benzodiazepin-3-yl)-2-(2,4-bis(trifluoromethyl)phenyl)acetamide

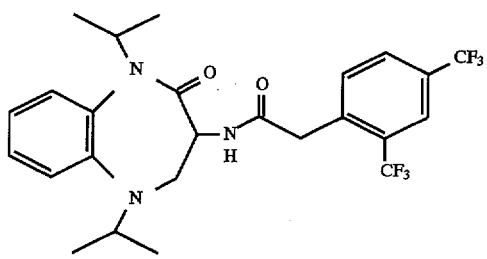

The synthesis of this compound is shown diagramatically in Scheme II and is fully explained in Example 6.

An other embodiment of the novel compounds of this invention is (+)-N-(2-Oxo-1,5-bis-(2-propyl)-2,3,4,5-tetrahydro-1H-1,5-benzodiazepin-3-yl)-2-(2,4-dichlorophenyl)acetamide which is also known as (+)-2-(2,4-Dichloro-phenyl)-N-[2-oxo-1,5-diisopropyl-2,3,4,5-tetrahydro-1H-benzo[b][1,4]diazepin-3-yl]-acetamide

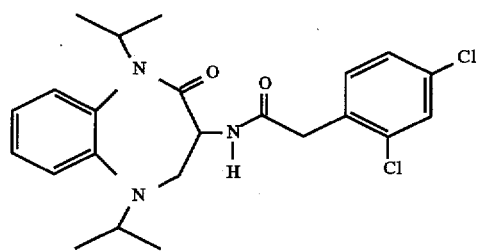

The synthesis for which is fully expalined in Example 7.

Yet another example of the compounds of this invention is (+)-N-(2-Oxo-1,5-bis-(2-propyl)-2,3,4,5-tetrahydro-1H-1,5-benzodiazepin-3-yl)-2-(3,5-dichlorophenyl)acetamide which is also known as (+)-2-(3,5-Dichloro-phenyl)-N-[2-oxo-1,5-diisopropyl-2,3,4,5-tetrahydro-1H-benzo[b][1,4]diazepin-3-yl]-acetamide

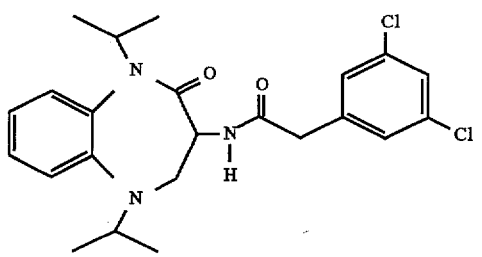

The synthesis for this compound can be found in Example 8.

Still an other example of the compounds of this invention is (+)-N-(2-Oxo-1-(2-propyl)-5-(2-propyl)-2,3,4,5-tetrahydro-1H-1,5-benzodiazepin-3-yl)-2-(2,4-bis(trifluoromethyl)phenyl)acetamide alternative naming:

(+)-2-(2,4-trifluoromethyl-phenyl)-N-[2-oxo-1,5-diisopropyl-2,3,4,5-tetrahydro-1H-benzo[b][1,4]diazepin-3-yl]-acetamide

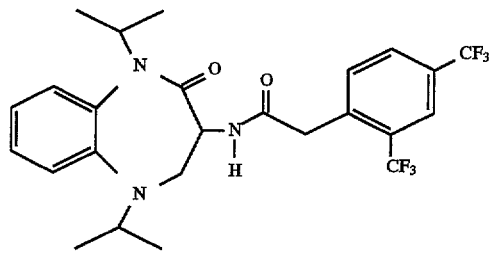

The synthesis for this compound and compounds like it can be found in Example 9.

In still an other embodiment of the novel compounds of this invention is (−)-N-(4-Oxo-1-(2-propyl)-5-(2,2,2-trifluoroethyl)-2,3,4,5-tetrahydro-1H-1,5-benzodiazepin-3-yl)-2-(2,4-dichlorophenyl)acetamide

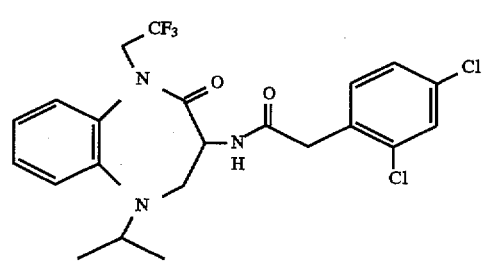

The synthesis of this compound is shown diagramatically in Scheme III and is fully explained in Example 10.

An other embodiment of the novel compounds of this invention is (−)-N-(4-Oxo-1-(2-propyl)-5-(2,2,2-trifluoroethyl)-2,3,4,5-tetrahydro-1H-1,5-benzodiazepin-3-yl)-2-(2,4-bis(trifluoromethyl)phenyl)acetamide

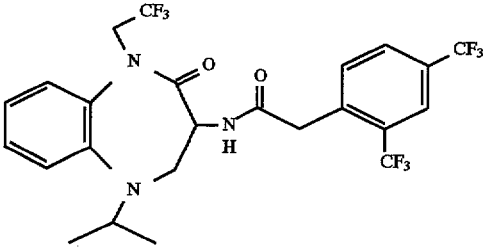

The synthesis of this compound is shown diagramatically in Scheme III and is fully explained in Example 11.

An other embodiment of the compounds of this novel invention is (+)-N-(4-Oxo-1-(2-propyl)-5-(2,2,2-trifluoroethyl)-2,3,4,5-tetrahydro-1H-1,5-benzodiazepin-3-yl)-2-(2,4-dichlorophenyl)acetamide

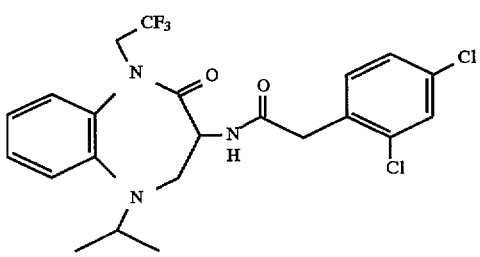

The synthesis of this compound is shown diagramatically in Scheme III and is fully explained in Example 12.

Still an other embodiment of this invention is (+)-N-(4-Oxo-1-(2-propyl)-5-(2,2,2-trifluoroethyl)-2,3,4,5-tetrahydro-1H-1,5-benzodiazepin-3-yl)-2-(2,4-bis(trifluoromethyl)phenyl)acetamide

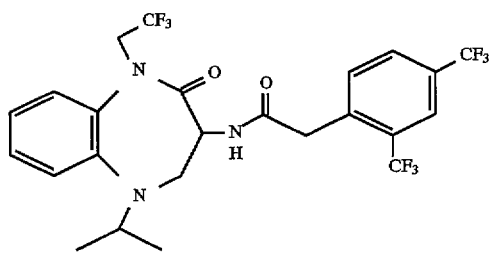

The synthesis of this compound is shown diagramatically in Scheme III and is fully explained in Example 13.

Yet an other embodiment of the novel compounds of this invention is 2-(2,4-Dichlorophenyl)-N-(1,5-bis-isopropyl-2,3,4,5-tetrahydro-1H-benzo[b][1,4]diazepin-3-yl)-acetamide

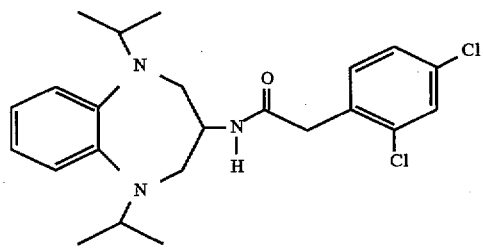

The synthesis of this compound is shown diagramatically in Scheme IV and is fully explained in Example 14.

An other embodiment of the compounds of this invention is 2-(2,4-bis-Trifluoromethylphenyl)-N-(1,5-bis-isopropyl-2,3,4,5-tetrahydro-1H-benzo[b][1,4]diazepin-3-yl)-acetamide

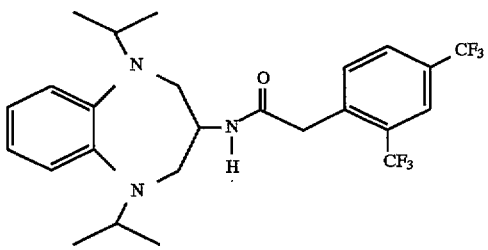

The synthesis of this compound is shown diagramatically in Scheme IV and is fully explained in Example 15.

The novel processes for preparing the compounds of this invention are schematically exemplified below in schemes I, II, III and IV. These steps are known in the art and/or described in the Examples that follow.

Scheme I

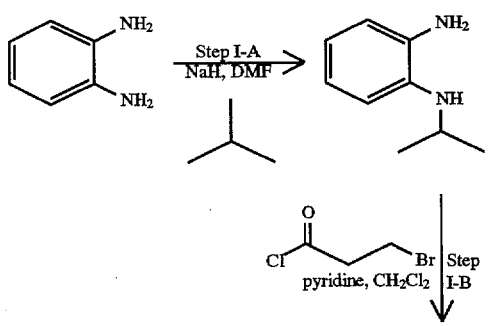

The novel compounds of the present invention, have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 5.0 mg per kg of body weight per day in a single dose or in 2 to 4 divided doses.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, emulsions, syrups, wafers, chewing gum, or the like prepared by art recognized procedures. The amount of active compound in such therapeutically useful compositions or preparations is such that a suitable dosage will be obtained.

These compounds can be administered as the sole active ingredient or in combination with other antiarrhythmic agents or other cardiovascular agents, such as Class I, Class II or Class IV antiarrhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

By Class I antiarrhythmic agents is meant those agents which provide for sodium channel blockade, including those compounds which exert a membrane stabilizing effect. Exemplary of this class of compounds are quinidine, procainamide, disopyrmmide, lidocane, tocainide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention, compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993, which is hereby incorporated by reference.

Exemplary of vasodilators are compounds such as papaverine and isosorbide dinitrat. Examples of angiotensin converting enzyme inhibitors include enalapril, lisinopril and captopril. Examples of diuretics include hydrochlorothiazide and acetazolamide. The pharmaceutical agents listed herein are examples and do not represent a complete listing of the many compounds in these classes which are contemplated by this invention.

The activity of the compounds described herein as antiarrhythmic agents is measured by their ability to block the IKs and IKr currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier K$^+$ current: differential sensitivity to block by Class III antiarrhythmic agents. J. Gen Physiol. 96:195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4 KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). IKI is measured as peak outward current during the voltage ramp. IKr is measured as tail currents upon repolarization from −10 mV to −50 mV. IKs is measured as time-dependent current during the pulse to +50 mV. Currents are measured during control, then after exposure to drug at two different concentrations.

Employing this test the compounds described herein have an IC$_{50}$ of less than 1,000 nM as IKs blockers. The compounds of this invention are at least 10 times more potent in the blockade of IKs than the blockade of IKr.

EXAMPLES

In the following examples, reference is made to the steps outlined in the schemes found in the Detailed Description of the Invention. For example, "Step I-A" refers to Step A of Scheme I.

Example 1

N-(2-Oxo-1,5-bis-(2-propyl)-2,3,4,5-tetrahydro-1H-1,5-benzodiazepin-3-yl)-2-(2,4-dichlorophenyl) propionamide

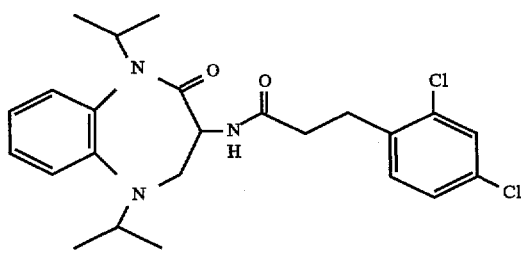

Step I-A: N-(2-Propyl)-phenylenediamine

A solution of o-phenylenediamine (10 g, 100 mmole) in acetonitrile (200 mL) was treated with 2-iodopropane (25.5 g, 150 mmole) and solid sodium hydrogen carbonate (10 g). The reaction was warmed to 80° C. and stirred for 5 hours. The reaction was cooled, poured into water (500 mL) and extracted with ethyl acetate (3 IV 200 mL). The organic layers were combined, dried over anhydrous magnesium sulfate, filtered, and concentrated in vacuo. The residue was chromatographed on silica gel eluting with 1:1 ethyl acetate-:hexane to give 5.7 g of the product and 7.8 g of the dialkylated material. $^1$H NMR (300 MHz, CDCl$_3$) d 6.85–6.75 (m, 1H), 6.6.75–6.60 (m, 3H), 3.60 (sep, J=7 Hz, 1H), 3.15 (br s, 3H), 1.21 (d, J=7 Hz, 6H).

Step I-B: N-(2-Propyl)-N'-(3-bromopropionyl)phenylene diamine

A solution of N-(2-propyl)-phenylenediamine (20 g, 0.133 mole) in methylene chloride (500 mL) at −78° C. was treated with pyridine (10.5 g, 0.133 mole) and then 3-bromopropionyl chloride (22.8 g, 0.133 mole). The reaction was warmed to ambient temperature and stirred for 2 hours. The reaction was poured into water (500 mL) and the layers were separated. The aqueous phase was extracted with ethyl acetate (200 mL). The organic layers were combined, dried over anhydrous magnesium sulfate, filtered, and concentrated in vacuo. The residue was chromatographed on silica gel eluting with 1:1 ethyl acetate:hexane and then triturated with ether to give 25 g of the product. The compound exists as a mixture of rotamers. The major rotamer has the following spectrum. $^1$H NMR (300 MHz, CDCl$_3$) d 7.40–7.05 (m, 2H),6.85–6.75 (m, 2H), 3.75 (t, J=7 Hz, 2H), 3.6 (m, 1H), 2.95 (t, J=7 Hz, 1H), 1.21 (d, J=7 Hz, 6H).

Step I—C: 1-Isopropyl-1,5-benzodiazepine-2-one

A solution of N-(2-propyl)-N'-(3-bromopropionyl) phenylenediamine (25 g, 0.087 mole) in tetrahydrofuran at 0° C. was treated with sodium hydride (3.8 g of 60% dispersion in mineral oil, 87.7 mmole). The reaction was stirred at 0° C. for 1 hour. Another equivalent of sodium hydride (3.8 g of 60% dispersion in mineral oil, 87 mmole) was then added and the reaction warmed to room temperature. The reaction was stirred at ambient temperature for 1 hour and then quenched by the careful addition of crushed ice. The reaction was poured into water (1.5 L) and the pH was adjusted to pH of 7 with dilute HCl. The aqueous mixture was extracted with ethyl acetate (3 IV 500 mL). The organic layers were combined, dried over anhydrous magnesium sulfate, filtered, and concentrated in vacuo. The residue was chromatographed on silica gel (0.75 kg) eluting with 1:1 ethyl acetate:hexane and then 100% ethyl acetate to give 12.6 g of the product as a viscous oil.

$^1$H NMR (300 MHz, CDCl$_3$) d 7.20–7.05 (m, 2H), 7.05–6.95 (m, 1H), 6.85–6.75 (m, 1H),4.73 (sep, J=7 Hz, 1H), 3.70 (m, 2H), 3.30 (m, 1H), 1.30 (m, 6H).

Step I-D: 1,5-Bis isopropyl-1,5-benzodiazepine-2-one

A solution of 1-isopropyl-1,5-benzodiazepine-2-one (12.6 g, 0.052 mole) in DMF was treated with solid sodium hydrogen carbonate (10 g, 0.11 mole) and 2-iodopropane (19.6 g, 0.11 mole). The reaction was heated to 80° C. for a total of 10 hrs, cooled to room temperature and poured into water (1 L). The aqueous mixture was extracted with ethyl acetate (3×300 mL) and the organic layers combined, dried over magnesium sulfate, filtered, and concentrated in vacuo. The crude material was chromatographed on silica gel (500 g) eluting with 3:7 ethyl acetate:hexanes to give 9.3 g of the product as an oil.

$^1$H NMR (300 MHz, CDCl$_3$) d 7.28–7.15 (m, 3H), 7.08–6.95 (m, 1H), 4.75 (sep, J=7 Hz, 1H), 3.70 (m, 1H), 3.55 (sep, J=7 Hz, 1H), 3.00 (m, 1H), 2.45–2.20 (m, 2H), 1.50–0.80 (m, 12H).

Step I-E: 3-Azido-1,5-Bis-2propyl-1,5-benzodiazepine-2-one

A solution of diisopropylamine (5.4 g, 53.5 mole) in tetrahydrofuran (300 mL) at −78° C. was treated with n-butyllithium(21 mL of a 2.5N solution in hexane, 0.053 mole) The solution was stirred at −78° C. for 5 minutes and then a solution of 1,5-Bis-2-propyl-1,5-benzodiazepine-2-one (11 g, 44.6 mole) in tetrahydrofuran (50 mL) was added slowly over 5 minutes. The resulting solution was allowed to stir at −78° C. for another 5 minutes at which time the triisopropylbenzenesulfonylazide (16.5 g, 0.053 mole) was added in tetrahydrofuran (50 mL). The reaction was stirred at −78° C. for 5 minutes and acetic acid was added to quench the reaction. The cold bath was removed and the reaction allowed to warm to room temperature over 1 hour. The reaction was poured into a solution of saturated sodium hydrogen carbonate (1 L) ethyl acetate (500 mL) was then added and the layers were separated. The aqueous phase was extracted with ethyl acetate (200 mL). The organic layers were combined, dried over anhydrous magnesium sulfate, filtered, and concentrated in vacuo. The residue was chromatographed on silica gel eluting with 1:3 ethyl acetate::hexane and then triturated with ether to give 6.1 g of the azide product.

$^1$H NMR (300 MHz, CDCl$_3$) d 7.30–7.15 (m, 3H), 7.07–7.00 (m, 1H), 4.73 (sep, J=7 Hz, 1H), 3.70–3.60 (m, 1H), 3.60–3.45 (m, 2H),3.30–3.20 (m, 1H), 1.42 (d, J=7 Hz, 3H), 1.29(d, J=7 Hz, 3H),1.08 (d, J=7 Hz, 6H).

Step I—F: 3-Amino-1,5-Bis-(2-propyl)-1,5-benzodiazepine-2-one

A solution of 3-azido-1,5-bis-(2-propyl)-1,5-benzodiazepine-2-one (9 g, mole) in tetrahydrofuran (200 mL) and treated with water (10 mL) and triphenylphosphine (16.4 g, 62.6 mole). The reaction was stirred overnight at room temperature and then poured into 1N HCl (1 L), ethyl ether (250 mL) was then added and the layers were separated. The aqueous phase was extracted with another portion of ethyl ether (50 mL). The ether fractions were discarded. The aqueous phase was basified to pH 9 and extracted with ethyl acetate (3 IV 200 mL). The organic layers were combined, dried over anhydrous magnesium sulfate, filtered, and concentrated in vacuo. The residue was chromatographed on silica gel eluting with 1:3 ethyl acetate:hexane and then triturated with ether to give 7.2 g of the amine.

$^1$H NMR (300 MHz, CDCl$_3$), d 7.30–7.15 (m, 3H), 7.07–7.00 (m, 1H), 4.75 (sep, J=7 Hz, 1H), 3.50 (sep, J=7 Hz, 1H), 3.35–3.26 (m, 1H), 3.20–3.15 (m, 2H), 1.40 (d, J=7 Hz, 3H), 1.25(d, J=7 Hz, 3H),1.04 (d, J=7 Hz, 6H).

Step I-G: N-(2-Oxo-1,5-bis(2-propyl)-2,3,4,5-tetrahydro-1H-1,5-benzodizepin-3-yl)-2-(2,4-dichlorophenyl) propionamide To a stirring solution of 3-amino-1,5-bis-(2-propyl)-1,5-benzodiazepine-2-one (100 mg, 0.38 mmol) in N,N-dimethylformamide (1 mL) was added 1-(3-Dimethylaminopropyl-3-ethylcarbodiimide (EDC, 88 mg, 0.46 mmol), 1-Hydroxybenztriazole hydrate (HOBT, 62 mg, 0.46 mmol) and 2,4-dichlorophenylpropionic acid (101 mg, 0.46 mmol). This was stirred at ambient temperature for 2 h. The reaction was diluted with saturated aqueous sodium hydrogen carbonate (100 mL) and extracted with ethyl acetate (3×50 mL). The organic layers were combined, dried with brine, anhydrous magnesium sulfate, filtered, and evaporated trader reduced pressure to give a colorless oil which was chromatographed over silica with 10 to 30% ethyl acetate/hexane. The resulting foam was crystallized from ethyl acetate/hexane to give a white solid (90 mg, 51%). mp=127°–128° C.

$^1$H NMR (300 MHz, CDCl$_3$), d 7.35–7.10 (m, 6H), 7.10–7.00 (m, 1H), 6.51 (d, J=6.9 Hz, 1H), 4.68 (septet, J=7.0 Hz, 1H), 4.43–4.35 (m 1H), 3.51 (septet, J=7.0 Hz, 1H), 3.40–3.30 (dd, J=7.0, 9.0 Hz, 1H), 3.05–2.95 (m, 3H), 2.52–2.45 (t, J=7.5 Hz, 1H), 1.40 (d, J=7.0 Hz, 3H), 1.23 (d, J=7.0 Hz, 3H), 1.06 (d, J=7.0 Hz, 3H), 1.03 (d, J=7.0 Hz, 3H).

Anal. Calcd. for $C_{24}H_{29}N_3O_2Cl_2$: C, 61.74; H, 6.37; N, 9.00. Found: C, 61.77; H, 6.27; N, 8.95.

The following examples were prepared by a procedure substantially as described above for Step I-G but substituting the appropriate carboxylic acid.

Example 2

N-(2-Oxo-1,5-bis-(2-propyl)-2,3,4,5-tetrahydro-1H-1,5-benzodiazepin-3-yl)-2-(3,5-dichlorophenyl)acetamide

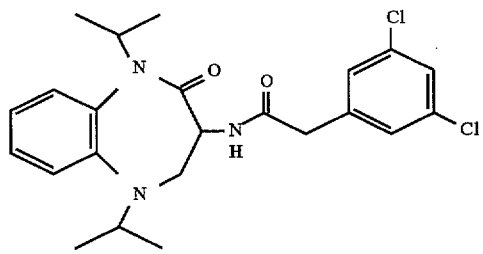

mp=165°–166° C.

$^1$H NMR (300 MHz, CDCl$_3$), d 7.40–7.14 (m, 6H), 7.10–7.00 (m, 1H), 6.70 (d, J=6.9 Hz, 1H), 4.71 (septet, J=6.8 Hz, 1H), 4.45–4.35 (m 1H), 3.50 (septet, J=6.8 Hz, 1H), 3.50–3.40 (m, 3H), 3.11 (dd, J=11, 9.0 Hz, 1H), 1.39 (d, J=6.7 Hz, 3H), 1.23 (d, J=6.8 Hz, 3H), 1.06 (d, J=6.8 Hz, 3H), 1.04 (d, J=6.7 Hz, 3H).

Anal. Calcd. for C$_{23}$H$_{27}$N$_3$O$_2$Cl$_2$•0.25H$_2$O: C, 61.00; H, 6.12; N, 9.28. Found: C, 61.06; H, 6.03; N, 9.11.

Example 3

N-(2-Oxo-1,5-bis-(2-propyl)-2,3,4,5-tetrahydro-1H-1,5-benzodiazepin-3-yl)-2-(2,4-dichlorophenyl)acetamide

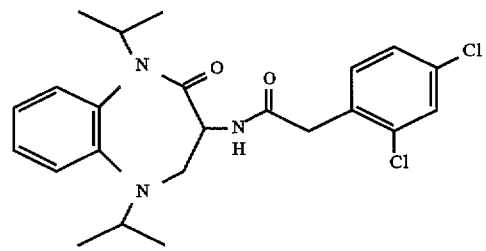

mp=139°–140° C.

$^1$H NMR (300 MHz, CDCl$_3$), d 7.41 (m,1H), 7.30–7.14 (m, 5H), 7.10–7.00 (m, 1H), 6.65 (br d, J=6.9 Hz, 1H), 4.71 (septet, J=6.8 Hz, 1H), 4.45–4.35 (m 1H), 3.63 (d, J=12 Hz, 1H), 3.59 (d, J=12 Hz, 1H), 3.52–3.40 (m, 2H), 3.08 (dd, J=11, 9.0 Hz, 1H), 1.39 (d, J=6.9 Hz, 3H), 1.23 (d, J=6.4 Hz, 3H), 1.04 (d, J=6.8 Hz, 3H), 1.03 (d, J=6.7 Hz, 3H).

Anal. Calcd. for C$_{23}$H$_{27}$N$_3$O$_2$Cl$_2$•0.10H$_2$O: C, 61.36; H, 6.09; N, 9.33. Found: C, 61.31; H, 6.04; N, 9.23.

Example 4

(−)-N-(2-Oxo-1,5-bis-(2-propyl)-2,3,4,5-tetrahydro-1H-1,5-benzodiazepin-3-yl)-2-(2,4-dichlorophenyl)acetamide

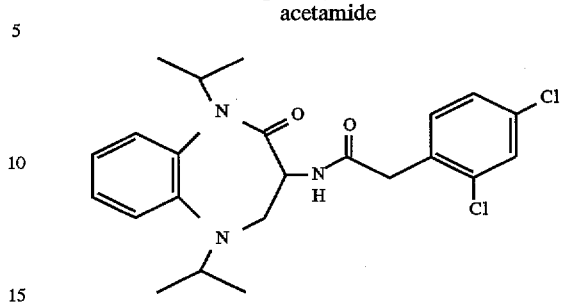

Step II-A: Preparation of (2R)-2-Amino-3-phenyl-N-[2,3-dihydro-1-(2-propyl)-2-oxo-5-(2-propyl)-1H-1,5-benzodiazepin-3-yl]propionamide To a stirring solution of (+)-3-Amino-2,3-dihydro-1-(2-propyl)-2-oxo-5-(2-propyl)-1H-1,5-benzodiazepine (7.0 g, 26.78 mmol) in dimethylformamide (500 mL) was added EDC (5.65 g, 29.46 mmol), HOBT (3.6 g, 26.78 mmol) and N-BOC-D-phenylalanine (7.81 g, 29.46 mmol). This was stirred at ambient temperature for 1 h. The reaction was diluted with saturated aqueous sodium hydrogen carbonate (0.5 L) and extracted with ethyl acetate (3×200 mL). The organic layers were combined, dried with brine, anhydrous magnesium sulfate, filtered, and evaporated under reduced pressure to give a yellow oil which was used without further purification The material thus obtained was dissolved in ethyl acetate (500 mL), cooled in an ice/water bath. Hydrogen chloride gas was bubbled into the solution for 1 h. The reaction mixture was concentrated under reduced pressure and the resulting foam was dissolved in ethyl acetate (200 mL) and saturated aqueous sodium hydrogen carbonate (500 mL). The layers were separated and the aqueous layer was extracted with ethyl acetate again (2×200 mL). The organic layers were combined, dried with brine, anhydrous magnesium sulfate, filtered, and evaporated under reduced pressure to give a white solid, which was chromatographed over silica (0.75 kg) eluting with ethyl acetate. The faster running diastereomer was recovered as a pale yellow oil (3.6 g). $^1$H NMR, CDCl$_3$, d 8.12 (d, J=8.6 Hz, 1H), 7.64–7.25 (m, 9H), 4.69 (septet, J=7.0 Hz, 1H), 4.44 (dt, J=7, 11.5 Hz, 1H), 3.60–3.42 (m, 2H), 3.38 (dd, J=7, 7.2, 10.0 Hz, 1H), 3.15 (dd, J=4.2, 14.2 Hz, 1H), 3.07 (dd, J=10, 11 Hz, 1H), 2.75 (dd, J=10.0, 14.2 Hz, 1H), 1.55–1.39 (m, 5H), 1.39 (d, J=7.0 Hz, 1H), 1.25(d, J=7.0 Hz, 1H), 1.05 (d, J=7.0 Hz, 1H), 1.02 (d, J=7.0 Hz, 1H).

The slower running diastereomer was recovered as a pale yellow oil (3.1 g) $^1$H NMR, CDCl$_3$, d 7.90 (d, J=8.5 Hz, 1H), 7.35 –7.15 (m, 8H), 7.06 (m, 1H) 4.68 (septet, J=7.0 Hz, 1H), 4.42 (dt, J=7, 11.5 Hz, 1H), 3.59–3.44 (m, 2H), 3.38 (dd, J=7, 7.2, 1H), 3.19 (dd, J=4.6, 14.2 Hz, 1H), 3.03 (dd, J=9.2, 11 Hz, 1H), 2.62 (dd, J=9.0, 14.2 Hz, 1H), 1.55–1.39 (m, 5H), 1.40 (d, J=7.0 Hz, 1H), 1.24 (d, J=7.0 Hz, 1H), 1.06 (d, J=7.0 Hz, 1H), 1.03 (d, J=7.0 Hz, 1H).

Step II-B: Preparation of (−)-3-Amino-2,3-dihydro-1-(2-propyl)-2-oxo-5-(2-propyl)-1H-1,5-benzodiazepine To a stirring solution of (2R)-2-Amino-3-phenyl-N-[2,3-dihydro-1-(2-propyl)-2-oxo-5-(2-propyl)-1H-1,4-benzodiazepin-3-yl]propionamide (3.5 g, 8.56 mmol) in methylene chloride (20 mL) was added phenylisothiocyanate (1.12 mL, 59.9 mmol) and the resulting solution was stirred for 16 h. The reaction mixture was concentrated under reduced pressure to yield a yellowish oil which was cooled in an ice/water bath. Trifluoroacetic acid (40 mL, 500 mmol) was added dropwise to the oil and the resulting solution was allowed to warm to ambient temperature over 2.5 h. The reaction mixture was concentrated under reduced pressure to yield a yellowish oil which was chromatographed over silica (1 kg) with 90:10:1:1 methylene chloride:methanol:acetic acid:water. The pure fractions were combined and washed with a solution of saturated sodium bicarbonate, dried over anhydrous magnesium sulfate, filtered and concentrated to give 1.9 grams of the product (−) amine. $[a]_D=-6.2°$ (c=0.69, MeOH), $^1$H NMR (300 MHz, CDCl$_3$), d 7.30–7.15 (m, 3H), 7.07–7.00 (m, 1H), 4.75 (sep, J=7 Hz, 1H), 3.50 (sep, J=7 Hz, 1H), 3.35–3.26 (m, 1H), 3.20–3.15 (m, 2H), 1.40 (d, J=7 Hz, 3H), 1.25(d, J=7 Hz, 3H),1.04 (d, J=7 Hz, 6H).

The (+) enantiomer was prepared in the same way except starting with the slower running product of Step III-A. $[a]_D=+4.8°$ (c=0.99, MeOH), Step II-C: (−)-N-(2-Oxo-1,5-bis-(2-propyl)-2,3,4,5-tetrahydro-1H-1,5-benzodiazepin-3-yl)-2-(2,4-dichlorophenyl)acetamide To a stirring solution of (−)-3-amino-1,5-bis-(2-propyl)-1,5-benzodiazepine-2-one (100 mg, 0.38 mmol) in N,N-dimethylformamide (1 mL) was added 1-(3-Dimethylaminopropyl-3-ethylcarbodiimide (EDC, 88 mg, 0.46 mmol), 1-Hydroxybenztriazole hydrate (HOBT, 62 mg, 0.46 mmol) and 2,4-dichlorophenylacetic acid (101 mg, 0.46 mmol). This was stirred at ambient temperature for 2 h. The reaction was diluted with saturated aqueous sodium hydrogen carbonate (100 mL) and extracted with ethyl acetate (3×50 mL). The organic layers were combined, dried with brine, anhydrous magnesium sulfate, filtered, and evaporated under reduced pressure to give a colorless oil which was chromatographed over silica with 10 to 30% ethyl acetate/hexane. The resulting foam was crystallized from ethyl acetate/hexane to give a white foam. $[a]_D=-34°$ (c=1.05, MeOH)

$^1$H NMR (300 MHz, CDCl$_3$), d 7.41 (m, 1H), 7.30–7.14 (m, 5H), 7.10–7.00 (m, 1H), 6.65 (br d, J=6.9 Hz, 1H), 4.71 (septet, J=6.8 Hz, 1H), 4.45–4.35 (m 1H), 3.63 (d, J=12 Hz, 1H), 3.59 (d, J=12 Hz, 1H), 3.52–3.40 (m, 2H), 3.08 (dd, J=11, 9.0 Hz, 1H), 1.39 (d, J=6.9 Hz, 3H), 1.23 (d, J=6.4 Hz, 3H), 1.04 (d, J=6.8 Hz, 3H), 1.03 (d, J=6.7 Hz, 3H).

Anal. Calcd. for $C_{23}H_{27}N_3O_2Cl_2$: C, 61.61; H, 6.07; N, 9.37. Found: C, 61.54; H, 6.17; N, 9.41.

The following examples (stereo (−)) were prepared from the (−) product of step II-B by a procedure substantially as described for step II-C Example 5

(−)-N -(2-Oxo-1,5-bis-(2-propyl)-2,3,4,5-tetrahydro-1H-1,5-benzodiazepin-3-yl)-2-(3,5-dichlorophenyl)acetamide

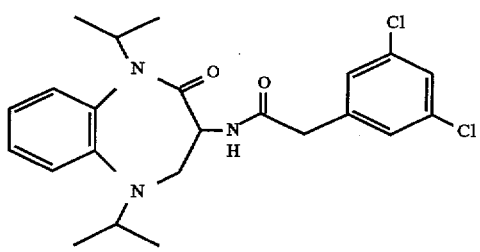

$[a]_D=-32°$ (c=0.65, MeOH)

$^1$H NMR (300 MHz, CDCl$_3$), d 7.40–7.14 (m, 6H), 7.10–7.00 (m, 1H), 6.70 (d, J=6.9 Hz, 1H), 4.71 (septet, J=6.8 Hz, 1H), 4.45–4.35 (m 1H), 3.50 (septet, J=6.8 Hz, 1H), 3.50–3.40 (m, 3H), 3.11 (dd, J=11, 9.0 Hz, 1H), 1.39 (d, J=6.7 Hz, 3H), 1.23 (d, J=6.8 Hz, 3H), 1.06 (d, J=6.8 Hz, 3H), 1.04 (d, J=6.7 Hz, 3H).

Anal. Calcd. for $C_{23}H_{27}N_3O_2Cl_2$: C, 61.61; H, 6.07; N, 9.37. Found: C, 61.75; H, 6.14; N, 9.51.

Example 6

(−)-N-(2-Oxo-1-(2-propyl)-5-(2-propyl)-2,3,4,5-tetrahydro-1H-1,5-benzodiazepin-3-yl)-2-(2,4-bis(trifluoromethyl)phenyl)acetamide

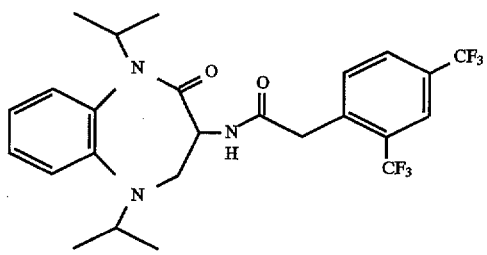

$[a]_D=-33°$ (c=0.95, MeOH)

$^1$H NMR (300 MHz, CDCl3), d 7.89 (s, 1H), 7.76 (d, J=7.9 Hz, 1H), 7.59 (d, J=7.9 Hz, 1H), 7.15–7.05 (m, 3H), 7.02 (t, J=7.6 Hz, 1H), 6.69 (br d, J=6.9 Hz, 1H), 4.71 (septet, J=6.8 Hz, 1H), 4.43–4.32 (m, 1H), 3.75 (s, 1H), 3.50 (septet, J=6.3 Hz, 1H), 3.41 (app t, J=7.0 Hz, 1H), 3.09 (app t, J=7.0 Hz, 1H), 1.39 (d, J=6.8 Hz, 3H), 1.23 (d, J=6.7 Hz, 3H), 1.04 (d, J=6.8 Hz, 3H), 1.03 (d, J=6.2 Hz, 3H).

Anal. Calcd. for $C_{25}H_{27}N_3O_2F_6$: C, 58.25; H, 5.28; N, 8.15. Found: C, 58.36; H, 5.31; N, 8.24.

The following examples (stereo (+)) were prepared from the (+) product of step II-B by a procedure substantially as described for step II-C Example 7

(+)-N-(2-Oxo-1,5-bis-(2-propyl)-2,3,4,5-tetrahydro-1H-1,5-benzodiazepin-3-yl)-2-(2,4-dichlorophenyl)acetamide alternative name:

(+)-2-(2,4-Dichloro-phenyl)-N-[2-oxo-1,5-diisopropyl-2,3,4,5-tetrahydro-1H-benzo[b][1,4]diazepin-3-yl]-acetamide

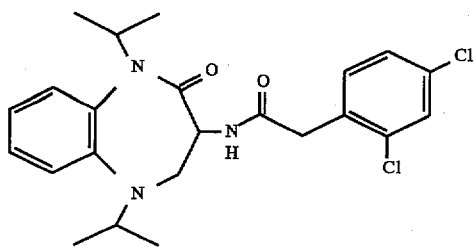

$[a]_d+30.7°$ (c=0.57,MeOH).

$^1$H NMR (CDCl$_3$, 300 MHz) d 7.41 (d,J=1.7 Hz,1H), 7.21 (m,5H), 7.04 (dxt,J=1.5 and 7.8 Hz,1H), 6.65 (d,J=6.6 Hz,1H), 4.71 (h,1H), 4.40 (dxt,J=11.0 and 6.8 Hz,1H), 3.62 (s,2H), 3.52 (h,J=6.4 Hz,1H), 3.44 (dxd,J=9.0 and 7.0 Hz,1H), 3.08 (dxd,J=11.0 and 7.0 Hz,1H), 1.38 (d,J=6.8 Hz,3H), 1.24 (d,J=6.4 Hz,3H), 1.04 (d,J=6.8 Hz,6H)

Anal. Calcd. for $C_{23}H_{27}Cl_2N_3O_2$: C, 61.61; H, 6.07; N, 9.37. Found: C, 61.6; H, 6.08; N, 9.15%.

Example 8

(+)-N-(2-Oxo-1,5-bis-(2-propyl)-2,3,4,5-tetrahydro-1H-1,5-benzodiazepin-3-yl)-2-(3,5-dichlorophenyl) acetamide alternative name:

(+)-2-(3,5-Dichloro-phenyl)-N-[2-oxo-1,5-diisopropyl-2,3,4,5-tetrahydro-1H-benzo[b][1,4]diazepin-3-yl]-acetamide

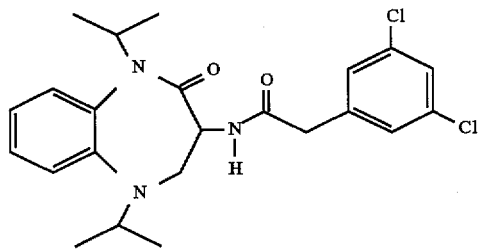

$[\alpha]_d = +33.4°$ (c=1.05,MeOH).

$^1$H NMR (CDCl$_3$, 300 MHz) d 7.27–7.03 (m,7H), 6.69 (d,J=6.1 Hz,1H), 4.71 (h,J=6.8 Hz,1H), 4.39 (ddd,J=6.9,6.7 and 10.9 Hz,1H), 3.51 (h,J=6.4 Hz,1H), 3.45 (s,2H), 3.43 (dd,J=8.9 and 6.9 Hz,1H), 3.10 (dd,J=10.9 and 8.9 Hz,1H), 1.39 (d,J=6.8 Hz,3H), 1.23 (d,J=6.4 Hz,3H), 1.05 (d,J=6.8 Hz,3H), 1.04 (d,J=6.4 Hz,3H)

Anal. Calcd. for $C_{23}H_{27}Cl_2N_3O_2$: C, 61.61; H, 6.07; N, 9.37. Found: C, 61.45; H, 6.02; N, 9.39%.

Example 9

(+)-N-(2-Oxo-1-(2-propyl)-5-(2-propyl)-2,3,4,5-tetrahydro-1H-1,5-benzodiazepin-3-yl)-2-(2,4-bis(trifluoromethyl)phenyl)acetamide alternative naming:

(+)-2-(2,4-trifluoromethyl-phenyl)-N-[2-oxo-1,5-diisopropyl-2,3,4,5-tetrahydro-1H-benzo[b][1,4]diazepin-3-yl]-acetamide

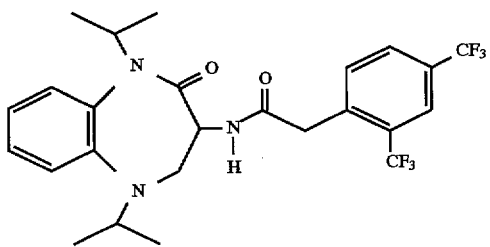

$[\alpha]_d = +33.7°$ (c=0.78,MeOH).

$^1$H NMR (CDCl$_3$, 300 MHz) d 7.90 (s,1H), 7.77 (d,J=8.1 Hz,1H), 7.60 (d,J=8.1 Hz,1H), 7.24–7.15 (m,2H), 7.05 (ddd, J=7.7,7.5 and 1.7 Hz,1H), 6.68 (d,J=6.7 Hz,1H), 4.71 (h,J= 6.8 Hz,1H), 4.39 (ddd,J=6.9,6.7 and 10.9 Hz,1H), 3.76 (s,2H), 3.50 (h,J=6.4 Hz,1H), 3.42 (dd,J=8.9 and 6.9 Hz,1H), 3.10 (dd,J=10.9 and 8.9 Hz,1H), 1.39 (d,J=6.8 Hz,3H), 1.23 (d,J=6.4 Hz,3H), 1.05 (d,J=6.8 Hz,3H), 1.04 (d,J=6.4 Hz,3H).

Anal. Calcd. for $C_{25}H_{27}F_6N_3O_2$: C, 58.25; H, 5.28; N, 8.15. Found: C, 57.99; H, 5.26; N, 8.06%.

Example 10

(−)-N-(4-Oxo-1-(2-propyl)-5-(2,2,2-trifluoroethyl)-2,3,4,5-tetrahydro-1H-1,5-benzodiazepin-3-yl)-2-(2,4-dichlorophenyl)acetamide

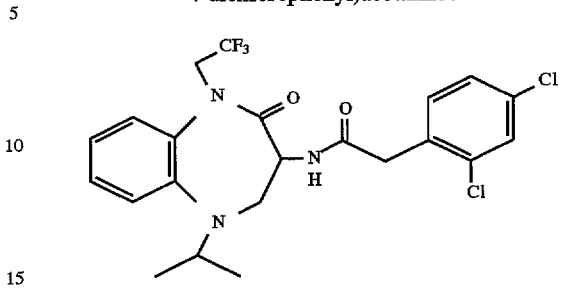

Step III-A: Methyl 2-benzyloxycarbonylamino-3-(2-nitrophenylamino)propionate

A stirring solution of 2-fluoronitrobenzene (1.83 mL, 17.3 mmole), methyl 2-carbobenzyloxyamino-3-aminopropionate hydrochloride (5.0 g, 17.3 mmole), and triethylamine (7.2 mL, 52 mmole) in N,N-dimethylformamide (40 mL) was heated at 70°–80° C. for five hours. The reaction mixture was cooled to ambient temperature, poured into saturated aqueous sodium hydrogen carbonate (300 mL) and extracted with ethyl acetate (3×200 mL). The organic layers were combined, dried over anhydrous magnesium sulfate, filtered and concentrated in vacuo. The residue was chromatographed on silica gel eluting with 3:17 ethyl acetate:hexane to give 5.4 g of product (83%).

$^1$H NMR (300 MHz, CDCl$_3$) d 8.27 (br s, 1H), 8.19 (d, J=8.0 Hz, 1H), 7.49–7.25 (m, 6H), 6.98 (d, J=8.0 Hz, 1H), 6.66 (t, J=8.0 Hz, 1H), 5.83 (d, J=6.4 Hz, 1H), 5.18 (s, 1H), 4.63 (dd, J=8.0 and 6.4 Hz, 1H), 4.90–4.73 (m, 5H).

Step III-B: Methyl 2-benzyloxycarbonylamino-3-(2-aminophenylamino)propionate

A stirring solution of methyl 2-benzyloxycarbonylamino-3-(2-nitrophenylamino)propionate (4.8 g, 12.9 mmole) and tin (II) chloride dihydrate 14.5 g, 64.3 mmole) in ethanol (50 mL) was heated at 70°–80° C. for five hours. The reaction mixture was cooled to ambient temperature, diluted with ethyl acetate (300 mL) poured into saturated aqueous sodium hydrogen carbonate (300 mL) and the resulting emulsion was filtered through Celite. The filtrate layers were separated and the aqueous layer was washed with ethyl acetate (2×100 mL). The organic layers were combined, dried over anhydrous magnesium sulfate, filtered and concentrated in vacuo. The residue was chromatographed on silica gel eluting with 2:3 ethyl acetate:hexane to give 3.0 g of product (68%). $^1$H NMR (300 MHz, CDCl$_3$) d 7.35 (s, 5H), 6.82–6.62 (m, 4H), 5.79 (d, J=7.3 Hz, 1H), 5.12 (s, 2H), 4.66 (br s, 1H), 3.75 (s, 3H), 3.65–3.40 (m, 4H).

Step III—C: 2-Benzyloxycarbonylamino-3-(2-aminophenylamino)propionic acid

To a stirring solution of methyl 2-benzyloxycarbonylamino-3-(2-aminophenylamino) propionate (3.0 g, 8.7 mmole) in tetrahydrofuran (30 mL) was added aqueous sodium hydroxide (1N, 13 mL). After stirring at ambient temperature for one hour, the reaction mixture was concentrated in vacuo. To the residue was added concentrated hydrochloric acid (12N, 1 mL), and aqueous sodium hydrogen phosphate, monobasic (1M, 500 mL), and this was extracted with ethyl acetate (3×200 mL). The organic layers were combined, dried over anhydrous magnesium sulfate, filtered and concentrated in vacuo. The resulting residue was utilized without further purification.

Step III-D: 3-Benzyloxycarbonylamino-1,5-benzodiazepine-2-one

To a stirring solution 2-benzyloxycarbonylamino-3-(2-amino-phenylamino)propionic acid in tetrahydrofuran (100 mL) was added 4-methylmorpholine (1.43 mL, 13.1 mmole). This reaction mixture was cooled in an ice/water bath and isobutyl chloroformate (1.69 mL, 13.1 mmole) was added dropwise. After addition was complete, the reaction mixture was warmed to ambient temperature over one hour. The reaction mixture was concentrated in vacuo and the resulting oil was dissolved in ethyl acetate (200 mL) and washed with saturated aqueous sodium hydrogen carbonate (300 mL). The aqueous layer was extracted with ethyl acetate (2×100 mL) and the organic layers were combined, dried over anhydrous magnesium sulfate, filtered and concentrated in vacuo. The residue was chromatographed on silica gel eluting with 1:1 ethyl acetate:hexane to give 2.3 g of product (85%). $^1$H NMR (300 MHz, CDCl$_3$) d 7.43–7.35 (m, 7H), 7.46–6.97 (m, 1H), 6.88–6.70 (m, 2H), 5.99 (d, J=6.7 Hz, 1H), 5.10 (s, 2H), 4.62–4.51 (m, 1H), 3.92 (dd, J=10.7 and 4.1 Hz, 1H), 3.45 (t, J=10.7 Hz, 1H).

Step III-E: 3-Benzyloxycarbonylamino-1-(2-propyl)-1,5-benzodiazepine-2-one

A stirring solution of 3-benzyloxycarbonylamino-1,5-benzodiazepine-2-one (2.3 g, 7.4 mmole), sodium hydrogen carbonate (6.2 g, 74 mmole) and 2-iodopropane (7.4 mL, 74 mmole) in N,N-dimethylformamide (12 mL) was heated to 50°–60° C. for 30 hours. The reaction mixture was cooled to ambient temperature, poured into saturated aqueous sodium hydrogen carbonate (250 mL) and extracted with ethyl acetate (3×150 mL). The organic layers were combined, dried over anhydrous magnesium sulfate, filtered and concentrated in vacuo. The residue was chromatographed on silica gel eluting with 1:4 ethyl acetate:hexane to give 2.2 g of product (84%). $^1$H NMR (300 MHz, CDCl$_3$) d 7.76 (br d, J=13 Hz, 1H), 7.34 (s, 5H), 7.18–7.10 (m, 2H), 6.98–6.80 (m, 2H), 5.85 (d, J=6.3 Hz, 1H), 5.07 (s, 2H), 4.53–4.82 (m, 2H), 3.78–3.60 (m, 2H), 3.30 (t, J=10.5 Hz, 1H), 1.31 (d, J=6.5 Hz, 3H), 1.14 (d, J=6.5 Hz, 3H).

Step III-F: 3-Benzyloxycarbonylamino-1-(2-propyl)-5-(2,2,2-trifluoroethyl)-1,5-benzodiazepine-2-one A stirring solution of 3-benzyloxycarbonylamino-1-(2-propyl)-1,5-benzodiazepine-2-one (2.2 g, 6.2 mmole), cesium carbonate (6.1 g, 18.7 mmole) and 2-iodo-1,1,1-trifluoroethane (3.1 mL, 31 mmole) in N,N-dimethylformamide (10 mL) was heated to 45°–50° C. for 12 hours. The reaction mixture was cooled to ambient temperature, poured into saturated aqueous sodium hydrogen carbonate (250 mL) and extracted with ethyl acetate (3×150 mL). The organic layers were combined, dried over anhydrous magnesium sulfate, filtered and concentrated in vacuo. The residue was chromatographed on silica gel eluting with 1:9 ethyl acetate: hexane to give 2.0 g of product (74%). $^1$H NMR (300 MHz, CDCl$_3$) d 7.39–7.04 (m, 9H), 5.72 (d, J=7.6 Hz, 1H), 5.04 (s, 2H), 4.94 (dq, J=15.1 and 8.6 Hz, 1H), 4.48–4.36 (m, 1H), 3.92 (dq, J=15.1 and 8.6 Hz, 1H), 3.61–3.43 (m, 2H), 3.26 (dd, J=11.3 and 11.1 Hz, 1H), 1.26 (d, J=6.4 Hz, 3H), 1.05 (d, J=6.4 Hz, 3H).

Step III-G: 3-Amino-1-(2-propyl)-5-(2,2,2-trifluoroethyl)-1,5-benzodiazepine-2-one 3-Benzyloxycarbonylamino-1-(2-propyl)-5-(2,2,2-trifluoroethyl)-1,5-benzodiazepine-2-one (1.8 g) was dissolved in 30% hydrobromic acid in acetic acid (8 mL). After one hour, the mixture was diluted with hydrochloric acid (1N, 300 mL) and extracted with diethyl ether (2×50 mL). The aqueous layer was basified with concentrated aqueous sodium hydroxide (50%) to pH 14 and then buffered to pH 10 with saturated aqueous sodium hydrogen carbonate (50 mL), which was then extracted with ethyl acetate (2×200 mL). The organic layers were combined, dried over anhydrous magnesium sulfate, filtered and concentrated in vacuo yielding 1.1 g of the amine as a colorless oil (88%). $^1$H NMR (300 MHz, CDCl$_3$) d 7.39–7.04 (m, 4H), 4.90 (dq, J=15.1 and 8.5 Hz, 1H), 3.96 (dq, J=15.1 and 8.5 Hz, 1H), 3.60–3.42 (m, 2H), 3.29 (dd, J=9.3 and 6.8 Hz, 1H), 3.21 (dd, J=11.4 and 9.5 Hz, 1H), 1.78 (br s, 2H), 1.27 (d, J=6.4 Hz, 3H), 1.05 (d, J=6.4 Hz, 3H).

The product of Step III-G, 3-Amino-1-(2-propyl)-5-(2,2,2-trifluoroethyl)-1,5-benzodiazepine-2-one, was resolved into its (+) and (−) enantiomers by the method depicted in scheme IV, to give the positive enantiomer [a]$_D$=+77 ° and the negative enantiomer [a]$_D$=−76°. The following examples were prepared from the individual enantiomers by the method of step II-C.

From the negative (−) enantiomer was prepared:

(−)-N-(4-Oxo-1-(2-propyl)-5-(2,2,2-trifluoroethyl)-2,3,4,5-tetrahydro-1H-1,5-benzodiazepin-3-yl)-2-(2,4-dichlorophenyl)acetamide

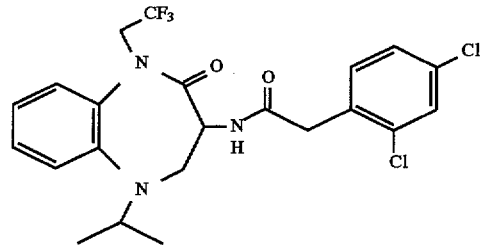

[a]$_D$=−87° (c=0.45; MeOH).

$^1$H NMR (CDCl$_3$) d 7.42 (s, 1H), 7.28–7.20 (m, 4H), 7.15–7.05 (m, 2H), 6.51 (d, J=7.0 Hz, 1H), 4.94 (dq, J=15.2 and 8.4 Hz, 1H), 4.60 (ddd, J=11.0, 9.0, and 7.0 Hz, 1H), 3.89 (dq, J=15.2 and 8.1 Hz, 1H), 3.64 (d, J=3.5 Hz, 1H), 3.59–3.42 (m, 2H), 3.18 (dd, J=11.0 and 9.0 Hz, 1H), 1.25 (d, J=6.5 Hz, 3H), 1.04 (d, J=6.5 Hz, 3H)

Anal. Calcd. for C$_{22}$H$_{22}$N$_3$O$_2$F$_3$Cl$_2$: C, 54.11; H, 4.54; N, 8.6. Found: C, 54.14; H, 4.65; N, 8.31%.

Example 11

(−)-N-(4-Oxo-1-(2-propyl)-5-(2,2,2-trifluoroethyl)-2,3,4,5-tetrahydro-1H-1,5-benzodiazepin-3-yl)-2-(2,4-bis(trifluoromethyl)phenyl)acetamide

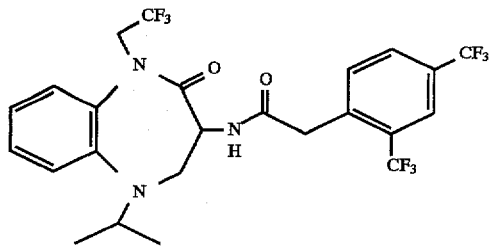

[a]$_D$=−77° (c=0.46; MeOH).

$^1$H NMR (CDCl$_3$) d 7.91 (s, 1H), 7.78 (d, J=8.1 Hz, 1H), 7.58 (d, J=7.8 Hz, 1H), 7.26–7.08 (m, 4H), 6.54 (d, J=6.6 Hz, 1H), 4.94 (dq, J=15.1 and 8.5 Hz, 1H), 4.59 (ddd, J=11.0, 9.0, and 7.1 Hz, 1H), 3.91 (dq, J=15.1 and 8.3 Hz, 1H), 3.77 (s, 1H), 3.58–3.43 (m, 2H), 3.19 (dd, J=11.0 and 9.3 Hz, 1H), 1.24 (d, J=6.3 Hz, 3H), 1.04 (d, J=6.3 Hz, 3H)

Anal. Calcd. for $C_{24}H_{22}N_3O_2F_9$: C, 51.9; H, 3.99; N, 7.57. Found: C, 52.17; H, 4.03; N, 7.54%. From the positive (+) enantiomer was prepared:

Example 12

(+)-N-(4-Oxo-1-(2-propyl)-5-(2,2,2-trifluoroethyl)-2,3,4,5-tetrahydro-1H-1,5-benzodiazepin-3-yl)-2-(2,4-dichlorophenyl)acetamide

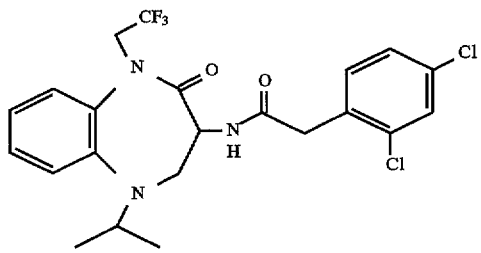

$[a]_D=+89°$ (c=0.44; MeOH).

$^1$H NMR (CDCl$_3$) d 7.42 (s, 1H), 7.28–7.20 (m, 4H), 7.15–7.05 (m, 2H), 6.51 (d, J=7.0 Hz, 1H), 4.94 (dq, J=15.2 and 8.4 Hz, 1H), 4.60 (ddd, J=11.0, 9.0, and 7.0 Hz, 1H), 3.89 (dq, J=15.2 and 8.1 Hz, 1H), 3.64 (d, J=3.5 Hz, 1H), 3.59–3.42 (m, 2H), 3.18 (dd, J=11.0 and 9.0 Hz, 1H), 1.25 (d, J=6.5 Hz, 3H), 1.04 (d, J=6.5 Hz, 3H)

Anal. Calcd. for $C_{22}H_{22}N_3O_2F_3Cl_2$: C, 54.11; H, 4.54; N, 8.6. Found: C, 54.27; H, 4.66; N, 8.5%.

Example 13

(+)-N-(4-Oxo-1-(2-propyl)-5-(2,2,2-trifluoroethyl)-2,3,4,5-tetrahydro-1H-1,5-benzodiazepin-3-yl)-2-(2,4-bis(trifluoromethyl)phenyl)acetamide

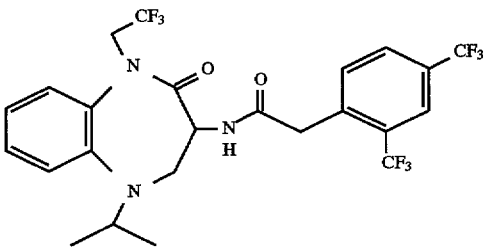

$[a]_D=+83°$ (c=0.49; MeOH).

$^1$H NMR (CDCl$_3$) d 7.91 (s, 1H), 7.78 (d, J=8.1 Hz, 1H), 7.58 (d, J=7.8 Hz, 1H), 7.26–7.08 (m, 4H), 6.54 (d, J=6.6 Hz, 1H), 4.94 (dq, J=15.1 and 8.5 Hz, 1H), 4.59 (ddd, J=11.0, 9.0, and 7.1 Hz, 1H), 3.91 (dq, J=15.1 and 8.3 Hz, 1H), 3.77 (s, 1H), 3.58–3.43 (m, 2H), 3.19 (dd, J=11.0 and 9.3 Hz, 1H), 1.24 (d, J=6.3 Hz, 3H), 1.04 (d, J=6.3 Hz, 3H).

Anal. Calcd. for $C_{24}H_{22}N_3O_2F_9$:C, 51.9; H, 3.99; N, 7.57. Found: C, 52.08; H, 4.07; N, 7.45%.

The following examples rely upon Scheme V. Starting from the product of Step I-F (3-Amino-1,5-Bis-(2-propyl)-1,5-benzodiazepine-2-one) and using procedures known in the art, there was obtained the following examples.

Example 14

2-(2,4-Dichlorophenyl)-N-(1,5-bis-isopropyl-2,3,4,5-tetrahydro-1H-benzo[b][1,4]diazepin-3-yl)-acetamide

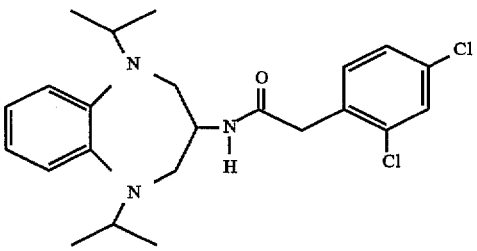

Anal. Calcd. for $C_{23}H_{29}N_3OCl_2.0.40$ mol $H_2O$: C, 62.56; H, 6.8; N, 9.52. Found: C, 62.57; H, 6.65; N, 9.41%.

Example 15

2-(2,4-bis-Trifluoromethylphenyl)-N-(1,5-bis-isopropyl-2,3,4,5-tetrahydro-1H-benzo[b][1,4]diazepin-3-yl)-acetamide

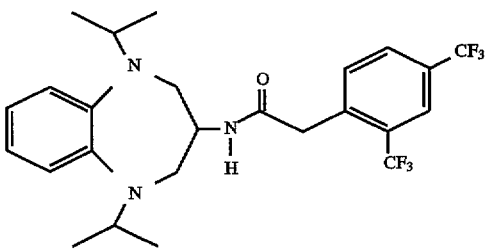

Anal. Calcd. for $C_{25}H_{29}N_3OF_6$: C, 59.87; H, 5.83; N, 8.38. Found: C, 59.59; H, 6.01; N, 8.53%.

What is claimed is:

1. A compound of the structural formula I

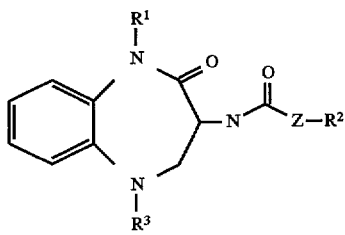

FORMULA I where

R$^1$ and R$^3$ are independently C$_{1-6}$ alkyl branched chain; substituted C$_{1-6}$alkyl branched chain wherein the substitutents are selected from F, C$_{3-8}$ cycloalkane, —OH, —CF$_3$, and Z is 1) C$_{1-6}$ alkyl, either straight or branch chain,
2) substituted C$_{1-6}$ alkyl, either straight or branch chain, wherein the substitutents are selected from F, —OH, NO$_2$,
2) C$_{2-4}$ alkenylene, either straight or branch chain,
3) —(CH$_2$)$_m$—W—(CH$_2$)$_n$— wherein m and n are independently 0, 1, 2, 3 or 4 and W is —O—, —S— or —NH,
4) C$_{3-6}$ cycloalkane,
5) C$_{3-6}$ cycloalkylene, or 6) single bond;
R² is
1) phenyl, either unsubstituted or substituted with one or two substituents selected from
   a) —NO₂, —OH
   b) —Cl, Br, F, or I,
   c) —CF₃,
   d) —$C_{1-3}$ alkyl,
   e) —$C_{1-3}$ alkoxy,
   f) —CN,
   g) -methylenedioxy,
$C_{5-7}$ cycloalkyl, either unsubstituted or substituted with one or two substitutents selected from
   a) —NO₂, —OH,
   b) F,
   c) —CF₃,
   d) —$C_{1-3}$ alkyl,
   e) —$C_{1-3}$ alkoxy,
   f) —CN,
   g) -methylenedioxy,
or pharmaceutically acceptable salts, hydrates and crystal forms thereof, which are useful as antiarrhythmic agents.

2. The compound of claim 1 which is N-(2-Oxo-1,5-bis-(2-propyl)-2,3,4,5-tetrahydro-1H-1,5-benzodiazepin-3-yl)-2-(2,4-dichlorophenyl)propionamide.

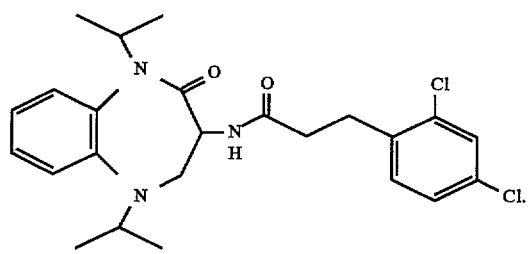

3. The compound of claim 1 which is N-(2-Oxo-1,5-bis-(2-propyl)-2,3,4,5-tetrahydro-1H-1,5-benzodiazepin-3-yl)-2-(3,5-dichlorophenyl)acetamide.

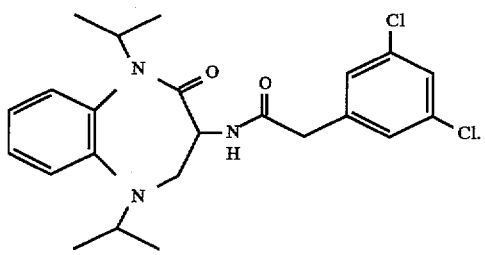

4. The compound of claim 1 which is N-(2-Oxo-1,5-bis-(2-propyl)-2,3,4,5-tetrahydro-1H-1,5-benzodiazepin-3-yl)-2-(2,4-dichlorophenyl)acetamide

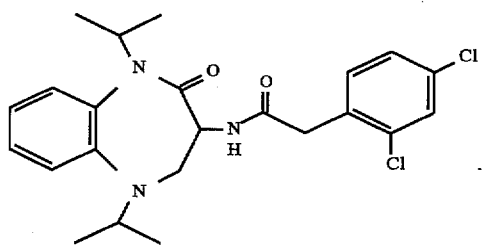

5. The compound of claim 1 which is (−)-N-(2-Oxo-1,5-bis-(2-propyl)-2,3,4,5-tetrahydro-1H-1,5-benzodiazepin-3-yl)-2-(2,4-dichlorophenyl)acetamide

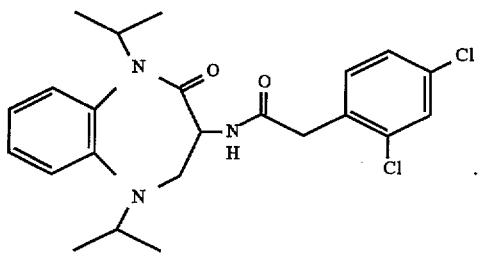

6. The compound of claim 1 which is (−)-N-(2-Oxo-1,5-bis-(2-propyl)-2,3,4,5-tetrahydro-1H-1,5-benzodiazepin-3-yl)-2-(3,5-dichlorophenyl)acetamide

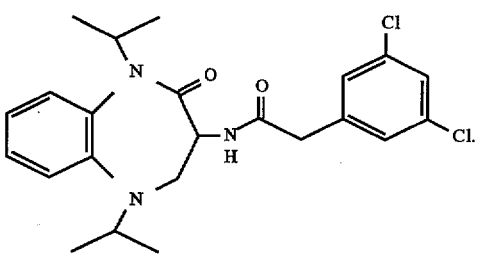

7. The compound of claim 1 which is (−)-N-(2-Oxo—1-(2-propyl)-5-(2-propyl)-2,3,4,5-tetrahydro-1H-1,5-benzodiazepin-3-yl)-2-(2,4-bis(trifluoromethyl)phenyl)acetamide

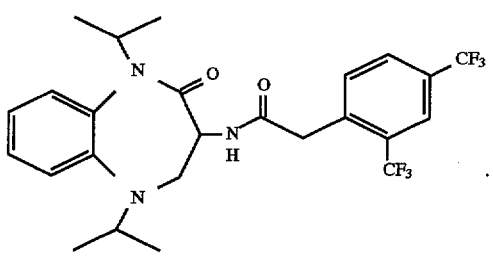

8. The compound of claim 1 which is (+)-N-(2-Oxo-1,5-bis-(2-propyl)-2,3,4,5-tetrahydro-1H-1,5-benzodiazepin-3-yl)-2-(2,4-dichlorophenyl)acetamide which is also known as (+)-2-(2,4-Dichlorophenyl)-N-[2-oxo-1,5-diisopropyl-2,3,4,5-tetrahydro-1H-benzo[b][1,4]diazepin-3-yl]-acetamide

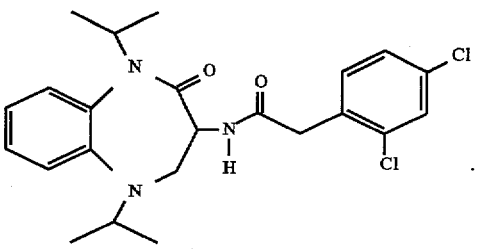

9. The compound of claim 1 which is (+)-N-(2-Oxo-1,5-bis-(2-propyl)-2,3,4,5-tetrahydro-1H-1,5-benzodiazepin-3-yl)-2-(3,5-dichlorophenyl)acetamide

27

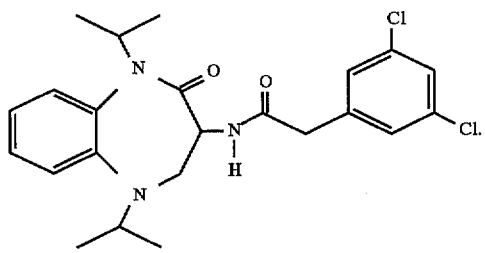

10. The compound of claim 1 which is (+)-N-(2-Oxo-1-(2-propyl)-5-(2-propyl)-2,3,4,5-tetrahydro-1H-1,5-benzodiazepin-3-yl)-2-(2,4-bis(trifluoromethyl)phenyl)acetamide

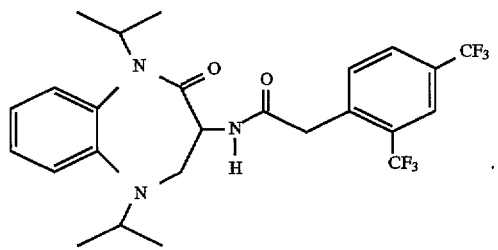

11. The compound of claim 1 which is (−)-N-(4-Oxo-1-(2-propyl)-5-(2,2,2-trifluoroethyl)-2,3,4,5-tetrahydro-1H-1,5-benzodiazepin-3-yl)-2-(2,4-dichlorophenyl)acetamide

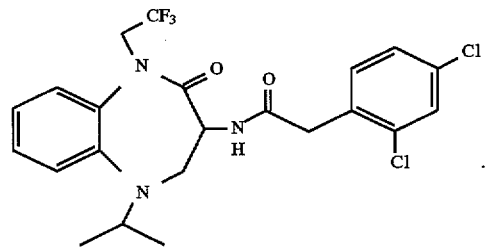

12. The compound of claim 1 which is (−)-N-(4-Oxo-1-(2-propyl)-5-(2,2,2-trifluoroethyl)-2,3,4,5-tetrahydro-1H-1,5-benzodiazepin-3-yl)-2-(2,4-bis(trifluoromethyl)phenyl)acetamide

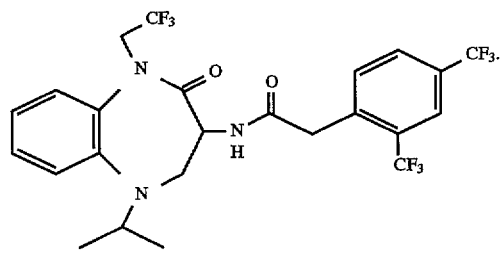

13. The compound of claim 1 which is (+)-N-(4-Oxo-1-(2-propyl)-5-(2,2,2-trifluoroethyl)-2,3,4,5-tetrahydro-1H-1,5-benzodiazepin-3-yl)-2-(2,4-dichlorophenyl)acetamide

28

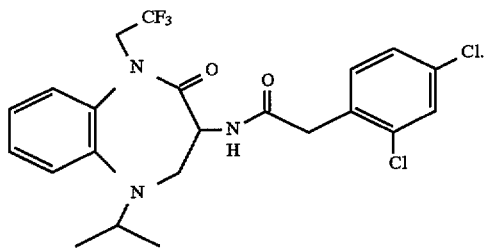

14. The compound of claim 1 which is (+)-N-(4-Oxo-1-(2-propyl)-5-(2,2,2-trifluoroethyl)-2,3,4,5-tetrahydro-1H-1,5-benzodiazepin-3-yl)-2-(2,4-bis(trifluoromethyl)phenyl)acetamide

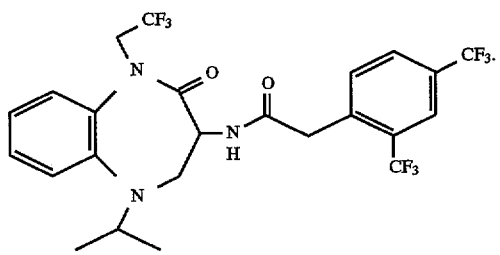

15. The compound of claim 1 which is 2-(2,4-Dichlorophenyl)-N-(1,5-bis-isopropyl-2,3,4,5-tetrahydro-1H-benzo[b][1,4]diazepin-3-yl)-acetamide

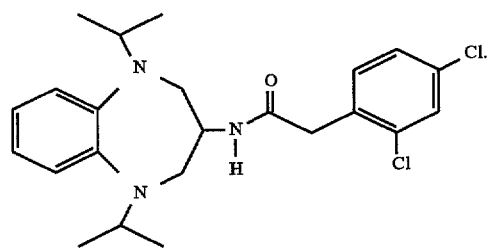

16. The compound of claim 1 which is 2-(2,4-bis-Trifluoromethylphenyl)-N-(1,5-bis-isopropyl-2,3,4,5-tetrahydro-1H-benzo[b][1,4]diazepin-3-yl)-acetamide,

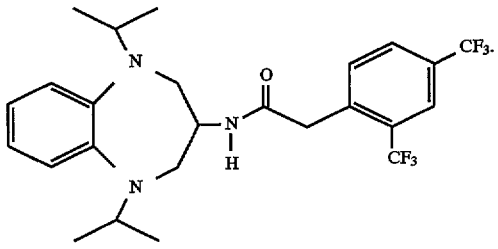

17. The compound of claim 1 selected from the group consisting of N-(2-Oxo-1,5-bis-(2-propyl)-2,3,4,5-tetrahydro-1H-1,5-benzodiazepin-3-yl)-2-(2,4-dichlorophenyl)propionamide,

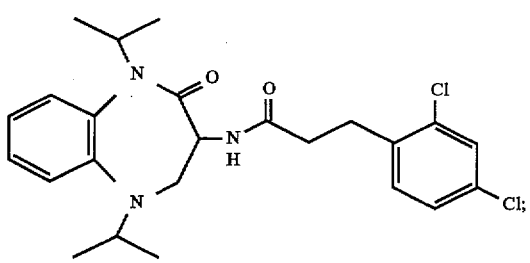

N-(2-Oxo-1,5-bis-(2-propyl)-2,3,4,5-tetrahydro-1H-
1,5-benzodiazepin-3-yl)-2-(3,5-dichlorophenyl)
acetamide,

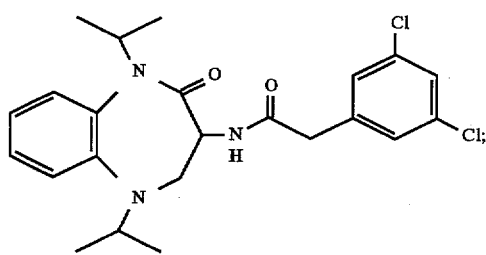

N-(2-Oxo-1,5-bis-(2-propyl)-2,3,4,5-tetrahydro-1H-
1,5-benzodiazepin-3-yl)-2-(2,4-dichlorophenyl)
acetamide

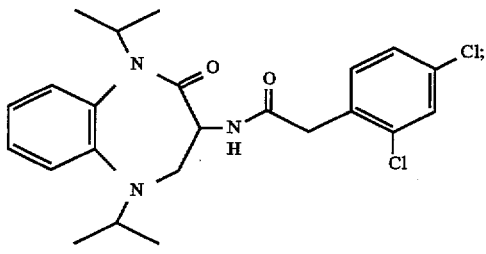

(−)-N-(2-Oxo-1,5-bis-(2-propyl)-2,3,4,5-tetrahydro-
1H-1,5-benzodiazepin-3-yl)-2-(2,4-dichlorophenyl)
acetamide

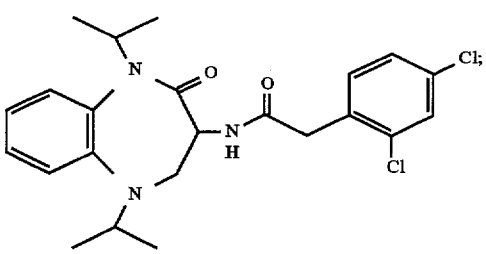

(−)-N-(2-Oxo-1,5-bis-(2-propyl)-2,3,4,5-tetrahydro-
1H-1,5-benzodiazepin-3-yl)-2-(3,5-dichlorophenyl)
acetamide

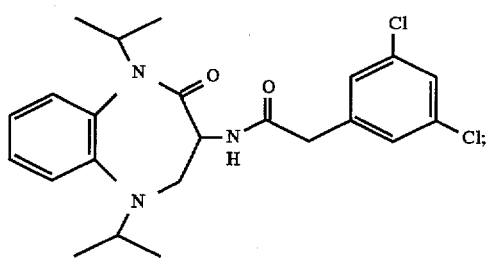

(−)-N-(2-Oxo-1-(2-propyl)-5-(2-propyl)-2,3,4,5-
tetrahydro-1H-1,5-benzodiazepin-3-yl)-2-(2,4-bis
(trifluoromethyl)phenyl)acetamide

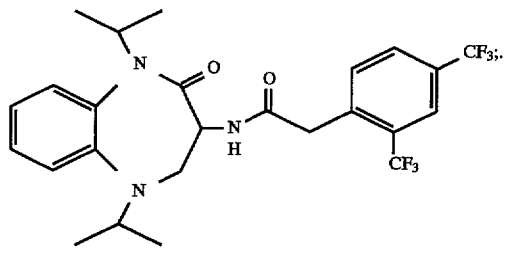

(+)-N-(2-Oxo-1,5-bis-(2-propyl)-2,3,4,5-tetrahydro-
1H-1,5-benzodiazepin-3-yl)-2-(2,4-dichlorophenyl)
acetamide

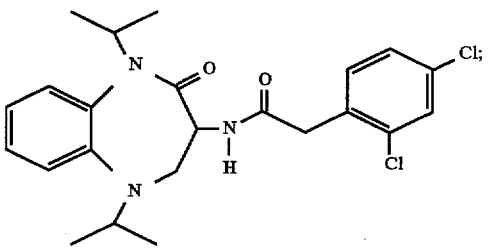

(+)-N-(2-Oxo-1,5-bis-(2-propyl)-2,3,4,5-tetrahydro-
1H-1,5-benzodiazepin-3-yl)-2-(3,5-dichlorophenyl)
acetamide

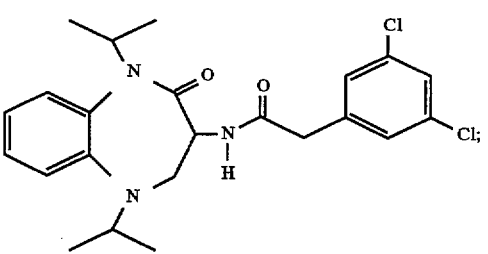

31

(+)-N-(2-Oxo-1-(2-propyl)-5-(2-propyl)-2,3,4,5-
tetrahydro-1H-1,5-benzodiazepin-3-yl)-2-(2,4-bis
(trifluoromethyl)phenyl)acetamide

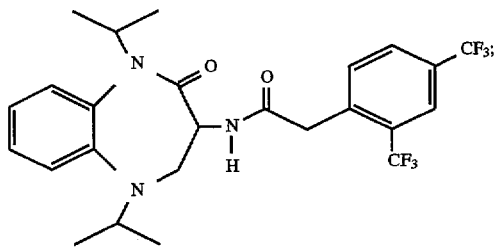

(−)-N-(4-Oxo-1-(2-propyl)-5-(2,2,2-trifluoroethyl)-2,
3,4,5-tetrahydro-1H-1,5-benzodiazepin-3-yl)-2-(2,4-
dichlorophenyl)acetamide

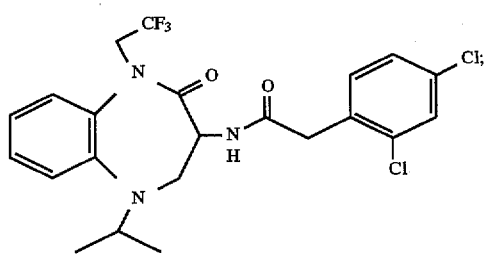

(−)-N-(4-Oxo-1-(2-propyl)-5-(2,2,2-trifluoroethyl)-2,
3,4,5-tetrahydro-1H-1,5-benzodiazepin-3-yl)-2-(2,4-
bis(trifluoromethyl)phenyl)acetamide

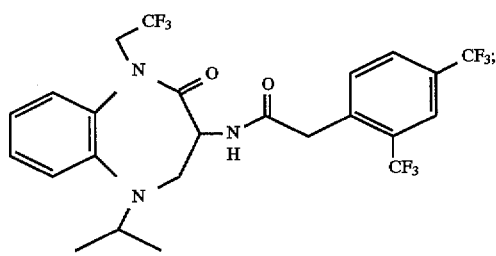

(+)-N-(4-Oxo-1-(2-propyl)-5-(2,2,2-trifluoroethyl)-2,
3,4,5-tetrahydro-1H-1,5-benzodiazepin-3-yl)-2-(2,4-
dichlorophenyl)acetamide

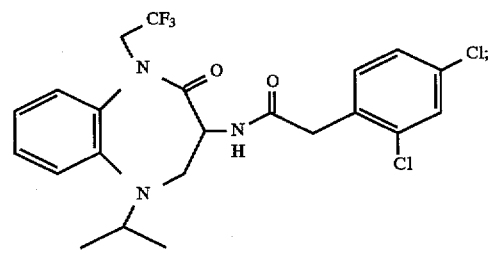

32

(+)-N-(4-Oxo-1-(2-propyl)-5-(2,2,2-trifluoroethyl)-2,
3,4,5-tetrahydro-1H-1,5-benzodiazepin-3-yl)-2-(2,4-
bis(trifluoromethyl)phenyl)acetamide

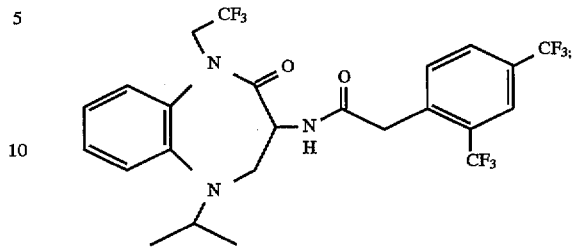

2-(2,4-Dichlorophenyl)-N-(1,5-bis-isopropyl-2,3,4,
5-tetrahydro-1H-benzo[b][1,4]diazepin-3-yl)-
acetamide

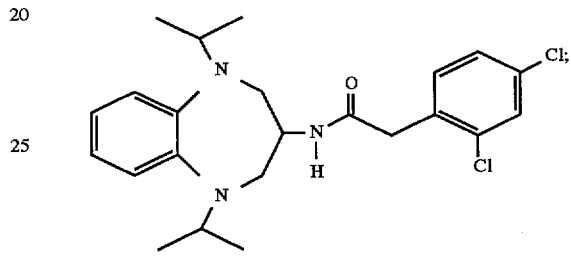

2-(2,4-bis-Trifluoromethylphenyl)-N-(1,5-bis-
isopropyl-2,3,4,5-tetrahydro-1H-benzo[b][1,4]
diazepin-3-yl)-acetamide

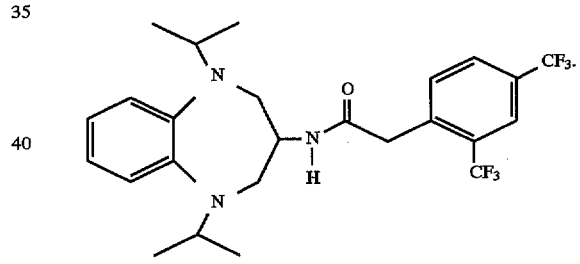

18. A pharmaceutical formulation comprising a pharmaceutically acceptable carrier and a therapeutically effective amount of the compound of claim 1 or a pharmaceutically acceptable salt, crystal form or hydrate thereof.

19. The pharmaceutical formulation of claim 18 comprising in addition another antiarrhythmic agent or other cardiovascular agent.

20. A method of preventing or treating arrhythmia which comprises the administration to a patient in need of such treatment of an antiarrhythmically effective amount of the compound of claim 1.

21. The method of claim 20 comprising the concomitant administration of another antiarrhythimic agent or other cardiovascular agent.

* * * * *